United States Patent
Sahin et al.

(10) Patent No.: US 11,510,891 B2
(45) Date of Patent: Nov. 29, 2022

(54) CAPE-LOADED TARGETED MICRO VESICULAR CANCER DRUG AND METHOD FOR DEVELOPING THE SAME

(71) Applicant: YEDITEPE UNIVERSITESI, Istanbul (TR)

(72) Inventors: Fikrettin Sahin, Istanbul (TR); Pakize Neslihan Tasli, Istanbul (TR); Oguz Kaan Kirbas, Istanbul (TR); Ezgi Avsar Apdik, Istanbul (TR); Huseyin Apdik, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 128 days.

(21) Appl. No.: 16/955,087

(22) PCT Filed: Dec. 17, 2018

(86) PCT No.: PCT/TR2018/050816
§ 371 (c)(1),
(2) Date: Jun. 18, 2020

(87) PCT Pub. No.: WO2019/132831
PCT Pub. Date: Jul. 4, 2019

(65) Prior Publication Data
US 2021/0023038 A1 Jan. 28, 2021

(30) Foreign Application Priority Data
Dec. 18, 2017 (TR) .................................. 2017/20642

(51) Int. Cl.
*A61K 31/216* (2006.01)
*A61K 9/127* (2006.01)
(52) U.S. Cl.
CPC .......... *A61K 31/216* (2013.01); *A61K 9/1277* (2013.01)

(58) Field of Classification Search
CPC ..................................................... A61K 31/216
See application file for complete search history.

(56) References Cited

U.S. PATENT DOCUMENTS

2011/0014251 A1 * 1/2011 Ray .................. A61P 19/10
424/401
2013/0315983 A1 * 11/2013 Einbond ............. A61K 45/06
514/274

(Continued)

FOREIGN PATENT DOCUMENTS

EP 1932517 A2 * 6/2008 .............. A61P 37/00

OTHER PUBLICATIONS

Hyo-Young Lee et al. "Preparation of Caffeic Acid Phenethyl Ester-Incorporated Nanoparticles and Their Biological Activity." Journal of Pharmaceutical Sciences, vol. 104, 2015, pp. 144-154. (Year: 2015).*

(Continued)

*Primary Examiner* — Isaac Shomer
(74) *Attorney, Agent, or Firm* — Bayramoglu Law Offices LLC

(57) ABSTRACT

A production of a drug, wherein the drug is specific for SH-SY5Y neuroblastoma cancer by loading caffeic acid phenethyl ester (CAPE) to a plurality of microvesicles that a specialized skin cell leaves into a nutrient solution. The objective of the present invention is to provide a cell-specific targeted vesicle development by loading the CAPE to the plurality of microvesicles obtained as a result of culturing and subsequent specialization of a plurality of tissue cells; and to use the CAPE at lower concentrations compared to a state of the art applications to minimize a toxicity of the CAPE to both a plurality of cells other than a plurality of targeted cells and a body.

3 Claims, 2 Drawing Sheets

(56) References Cited

U.S. PATENT DOCUMENTS

2016/0137716 A1* 5/2016 El Andaloussi .......... A61P 3/10
435/375
2017/0209499 A1* 7/2017 Suddes .................. A61K 47/40

OTHER PUBLICATIONS

Heikki Saari et al. "Microvesicle- and exosome-mediated drug delivery enhances the cytotoxicity of Paclitaxel in autologous prostate cancer cells." Journal of Controlled Release, vol. 220, 2015, pp. 727-737. (Year: 2015).*
Camilla Krizhanovskii et al. "EndoC—bH1 cells display increased sensitivity to sodium palmitate when cultured in DMEM/F12 medium." Islets, vol. 9 No. 3, 2017, pp. 43-48. (Year: 2017).*
Hiroshi Izuta et al. "Protective Effects of Chinese Propolis and its Component, Chrysin, against Neuronal Cell Death via Inhibition of Mitochondrial Apoptosis Pathway in SH—SY5Y Cells." Journal of Agricultural and Food Chemistry, vol. 56, 2008, pp. 8944-8953. (Year: 2008).*
Xiaoyang Zheng et al. "Proteomic Analysis for the Assessment of Different Lots of Fetal Bovine Serum as a Raw Material for Cell Culture. Part IV. Application of Proteomics to the Manufacture of Biological Drugs." Biotechnology Progress, vol. 22, 2006, pp. 1294-1300. (Year: 2006).*
Sreenivasa R. Chinni and Fazlul H. Sarkar. "Akt Inactivation is a Key Event in Indole-3-carbinol-induced Apoptosis in PC-3 Cells." Clinical Cancer Research, vol. 8, Apr. 2002, pp. 1228-1236. (Year: 2002).*
Kevin McEleny, Ronan Coffey, Colm Morrisey, John M. Fitzpatrick, and R. William G. Watson. "Caffeic acid phenethyl ester-induced PC-3 cell apoptosis is caspase-dependent and mediated through the loss of inhibitors of apoptosis proteins." BJU International, vol. 94, pp. 402-406. (Year: 2004).*
Heikki Saari, Elisa Lázaro-Ibáñez, Tapani Viitala, Elina Vuorimaa-Laukkanen, Pia Siljander, Marjo Yliperttula. "Microvesicle- and exosome-mediated drug delivery enhances the cytotoxicity of Paclitaxel in autologous prostate cancer cells." Journal of Controlled Release, vol. 220, 2015, pp. 727-737. (Year: 2015).*
Hui-Ping Lin et al., Caffeic Acid Phenethyl Ester as a Potential Treatment for Advanced Prostate Cancer Targeting Akt Signaling, International Journal of Molecular Sciences, 2013, pp. 5264-5283, vol. 14.
Mai F Tolba et al., Caffeic acid phenethyl ester: A review of its antioxidant activity, protective effects against ischemia-reperfusion injury and drug adverse reactions, 2014, pp. 1-27.
Jing Wu et al., Caffeic acid phenethyl ester (CAPE), derived from a honeybee product propolis, exhibits a diversity of anti-tumor effects in pre-clinical models of human breast cancer, Cancer Letters, 2011, pp. 43-53, 308.
Coral O Omene et al., Caffeic Acid Phenethyl Ester (CAPE) derived from propolis, a honeybee product, inhibits growth of breast cancer stem cells, Invest New Drugs, 2012, pp. 1279-1288, 30.
Chih-Pin Chuu et al., Caffeic Acid Phenethyl Ester Suppresses the Proliferation of Human Prostate Cancer Cells through Inhibition of p70S6K and Akt Signaling Networks, Cancer Prev Res, 2012, pp. 788-797, 5(5).
Tzu-Hui Hsu et al., Caffeic acid phenethyl ester induces E2F-1-mediated growth inhibition and cell-cycle arrest in human cervical cancer cells, FEBS Journal, 2013, 2581-2593, 280.
Ying-Yu Kuo et al., Caffeic Acid Phenethyl Ester Suppresses Proliferation and Survival of TW2.6 Human Oral Cancer Cells via Inhibition of Akt Signaling, International Journal of Molecular Sciences, 2013, pp. 8801-8817, 14.
Eun Young Kim et al., CAPE promotes TRAIL-induced apoptosis through the upregulation of TRAIL receptors via activation of p38 and suppression of JNK in SK-Hep1 hepatocellular carcinoma cells, International Journal of Oncology, 2013, pp. 1291-1300, 43.
Murat Yagmurca et al., Caffeic acid phenethyl ester as a protective agent against doxorubicin nephrotoxicity in rats, Clinica Chimica Acta, 2004, pp. 27-34, 348.
Ersin Fadillioglu et al., Protective Effects of Caffeic Acid Phenethyl Ester on Doxorubicin-induced Cardiotoxicity in Rats, Journal of Applied Toxicology, 2004, pp. 47-52, 24.
M Kemal Irmak et al., Effects of caffeic acid phenethyl ester and alpha-tocopherol on reperfusion injury in rat brain, Cell Biochem Funct, 2003, pp. 283-289, 21.
Mustafa Iraz et al., Protective effect of caffeic acid phenethyl ester (CAPE) administration on cisplatin-induced oxidative damage to liver in rat, Cell Biochem Funct, 2006, 357-361, 24.
Sumeyye Akyol et al., The potential usage of caffeic acid phenethyl ester (CAPE) against chemotherapy-induced and radiotherapy-induced toxicity. Cell Biochem Funct, 2012.
Oguz Galip Yildiz et al., Protective effects of caffeic acid phenethyl ester on radiation induced lung injury in rats, Clin Invest Med, 2008, E242-E247, vol. 31, No. 5.
Hiroshi Izuta et al., Protective Effects of Chinese Propolis and its Component, Chrysin, against Neuronal Cell Death via Inhibition of Mitochondrial Apoptosis Pathway in SH—SY5Y Cells, Journal of Agricultural and Food Chemistry, 2008, pp. 8944-8953, vol. 56, No. 19.
Hyo-Young Lee et al., Preparation of Caffeic Acid Phenethyl Ester-Incorporated Nanoparticles and Their Biological Activity, Journal of Pharmaceutical Sciences, 2015, pp. 144 154, 104.
Jane Kovalevich et al., Considerations for the Use of SH—SY5Y Neuroblastoma Cells in Neurobiology, Neuronal Cell Culture: Methods and Protocols, Methods in Molecular Biology, 2013, pp. 9-21, vol. 1078.
Ryoichi Tomiyama et al., 3,4-dihydroxybenzalacetone and caffeic acid phenethyl ester induce preconditioning ER stress and autophagy in SH—SY5Y cells, Journal of Cellular Physiology, 2017, pp. 1-37.

* cited by examiner

CAPE-LOADED TARGETED MICRO VESICULAR CANCER DRUG AND METHOD FOR DEVELOPING THE SAME

CROSS-REFERENCE TO THE RELATED APPLICATIONS

This application is the national stage entry of International Application No. PCT/TR2018/050816, filed on Dec. 17, 2018, which is based upon and claims priority to Turkish Patent Application No. 2017/20642, filed on Dec. 18, 2017, the entire contents of which are incorporated herein by reference.

TECHNICAL FIELD

The present invention relates to production of a drug which is specific for SH-SY5Y neuroblastoma cancer by loading CAPE to microvesicles that the specialized skin cell leaves into the medium.

BACKGROUND

CAPE (caffeic acid phenethyl ester) is one of the most widely studied active components of poplar type propolis. CAPE has antioxidant, antineoplastic, antitumoral and cytoprotective effects. CAPE inhibits carcinogenesis, cell cycle and metastasis, and induces apoptosis [1]. One of the interesting and important effects of CAPE is that when used with various antibiotics (streptomycin, vancomycin, isoniazid, ethambutol) and cancer drugs (mitomycin, doxorubicin, cisplatin, methotrexate); it reduces the toxicity occurring dependent on the said drugs [2].

It has been shown that CAPE (40 μM) dose-dependently stops cell proliferation, induces cell cycle arrest and apoptosis, and suppresses angiogenesis in estrogen receptor positive (ER+) MCF-7, estrogen receptor negative (ER−) MDA-MB-231, and triple negative (ER−, PR−, HER2−) TNBC breast cancer cell lines [3]. Additionally, it has also been determined that CAPE (40 μM) inhibits proliferation of breast cancer stem cells [4]. It has been shown that CAPE dose-dependently inhibits cell proliferation in LNCaP, DU-145 and PC-3 prostate cancer cell lines and Akt signaling pathway [5]. It has been demonstrated that CAPE (50 μM) prevents proliferation by inducing S and G2/M phase cell cycle arrests and induces apoptosis in the cells in ME180 cervical cancer cell lines [6]. It was determined that CAPE (100 μM) treatment decreased G1 phase cell population, increased G2/M phase cell population and induced apoptosis in the cells by inhibiting the Akt signaling pathway in TW2.6 oral squamous cell carcinoma cell line [7]. It has been determined that in the SK-1 Hep1 liver cancer cell line, to which combined treatment of CAPE (30 ug/ml) and TRAIL was applied, caspase activation increased, cell death receptors were activated via JNK and p38 signaling pathways and apoptosis was induced in the cells [8]. In the experimental studies, it was observed that CAPE inhibited the toxicity occurring during chemotherapy and radiotherapy. It is reported that the prophylactic administration of CAPE prevented the damage caused by doxorubicin in the tissues of kidney [9], heart [10] and brain [11], and the liver damage depending on administration of cisplatin [12] and tamoxifen [13] in rats. It has also been shown that CAPE treatment decreased radiation induced lung injury in rats [14]. In the study conducted with CAPE in SH-SY5Y neuroblastoma cell line, CAPE was applied in the range of 4-20 μM, but no effect was observed in the SH-SY5Y cells [15].

In another study, CAPE (100 μg/ml) was loaded in methoxy poly(ethylene glycol)-b-poly(ε-caprolactone) (CE) copolymer and it was applied in CT26 colon carcinoma cell line. When the results were compared with unaccompanied application of CAPE, no difference was observed on the effects thereof on cell proliferation and death [16].

The problems encountered in the state of the art applications can be listed as follows:
  Not being specific to the cell and tissue.
  Requirement to be used at high concentrations.
  Activation of mononuclear phagocyte system.
  Cancerous tissues showing chemical resistance in drug applications.

SUMMARY

The objective of the present invention is to provide a cell-specific targeted vesicle development by loading CAPE to the microvesicles obtained as a result of the culturing and subsequent specialization (differentiation) of the tissue cells.

Another objective of the invention is to use CAPE at lower concentrations compared to the state of the art applications to minimize its toxicity to both the cells other than the targeted cells and the body.

BRIEF DESCRIPTION OF THE DRAWINGS

"Development of a CAPE loaded microvesicular cancer drug targeting SH-SY5Y neuroblastoma cancer" developed to fulfill the objectives of the present invention is illustrated in the accompanying figures, in which.

DETAILED DESCRIPTION OF THE EMBODIMENTS

The invention is a cancer drug obtained by loading drug (CAPE) into the microvesicles produced by the differentiated skin stem cells, and it is applied due to the cytotoxic effect of these cellular vesicles on cancer cells. The drug is loaded to the vesicles of the cells, which are specialized by being treated with growth factors applied to provide nerve cell properties. Within the scope of the invention, the cells; which are differentiated by administering a Neurobasal solution preferably containing 10 ng/ml bFGF, 10 ng/ml EGF, 1% B7 supplement, 1% ITS (insulin, transferrin and selenium), 10% Glutamine and 1% PSA for 12-14 days; are provided with new properties by this method rendering the vesicles to target the SHSY5Y cancer cells. By means of the invention, the cellular vesicles are loaded with CAPE thereby acquiring the feature of specifically recognizing the SHSY5Y cancer cells.

Figure 1:
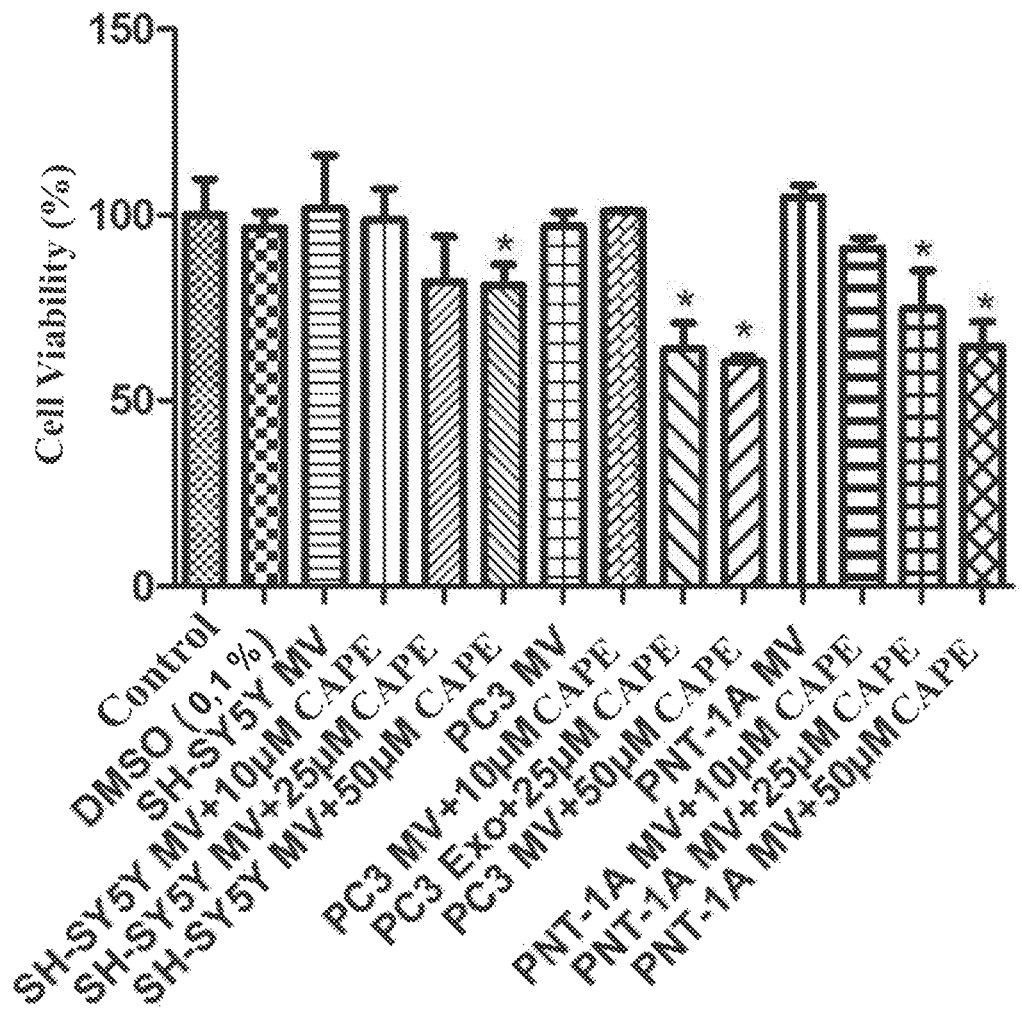
FIG. 1 is a graphical representation of the combinations formed by loading CAPE to the microvesicles obtained from SH-SY5Y, PC3 and PNT-1 cells on cell viability of SH-SY5Y cells in an application of 48 hours. (CAPE: Caffeic Acid Phenethyl Ester, MV: Microvesicle, *: P<0.05)
Figure 2:
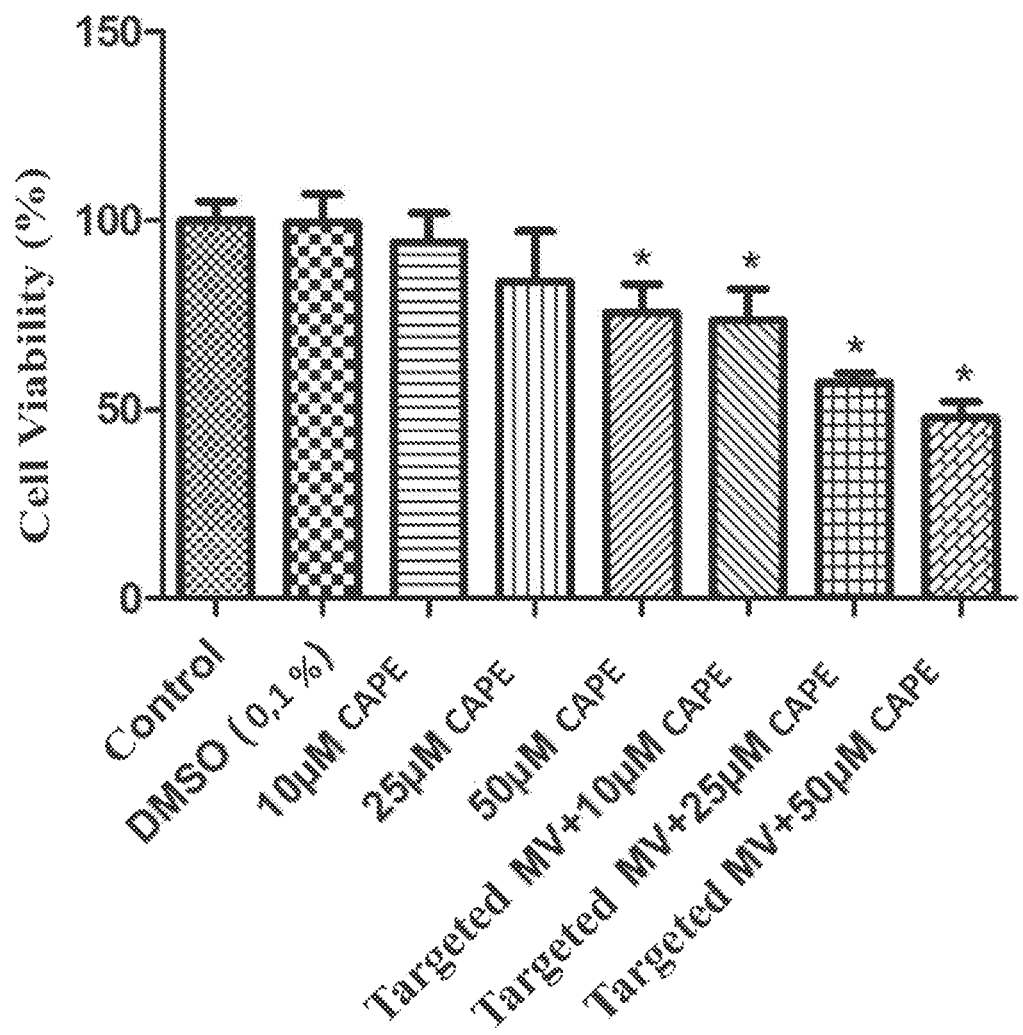
FIG. 2 is a graphical representation of the effect of the combinations obtained by loading different doses of CAPE (caffeic acid phenethyl ester) to the microvesicles obtained from the cells, which are differentiated from stem cells into healthy nerve cells, on cell viability of SH-SY5Y cells in an application of 48 hours. (CAPE: Caffeic Acid Phenethyl Ester, MV: Microvesicle, *: P<0.05)

There are two embodiments within the scope of the invention. In the first embodiment; by means of drug (CAPE (caffeic acid phenethyl ester) loading, cytotoxic property is provided to the cellular vesicles which are produced by changing the factors such as the temperature of 37° C., pH, 5% carbon dioxide and the DMEM, F12, RPMI media that enable cell growth, in addition to the growth conditions of the cells (stem cells, cell lines, primer cells, cancer cells, cells obtained from tissues). In the second embodiment; by means of drug (CAPE (caffeic acid phenethyl ester) loading, cytotoxic property is provided to the cellular vesicles which are produced by treating the cells (stem cells, cell lines, primer cells, cancer cells, cells obtained from tissues) with other chemicals (growth factors such as bFGF, EGF, NGF; hormones such as melatonin, insulin, lactoferrin; vitamins such as ascorbic acid, folic acid; and minerals such as calcium, magnesium, boron) in addition to the cells' own growth conditions. It has been observed that these vesicles, which are collected from the stem cells differentiated into nerve cells, while demonstrating a nerve cell recognition feature, they also exhibit cytotoxicity specific to SHSY5Y after treatment for 12-14 days as seen in FIG. 1. The term "specialized" is given as a result of the comparison of the SHSY5Y cell with the other cells as seen in FIG. 1.

In one embodiment of the invention, the microvesicles; which are produced by the cells specific to a particular cancer type by means of the differentiation of the cells to the tissue cells, where the said tumor formation is observed, acquired on the 12-14th days rather than 25-30 days; are used. Accordingly, the microvesicles produced by the cells are used because the specific characteristics of SHSY5Y cells, which are acquired by differentiation of the stem cells subjected to nerve cell differentiation, are carried in the early stage of nerve differentiation by differentiation at 12-14 days rather than 25-30 days.

In one embodiment of the invention, with the purpose of developing a CAPE loaded microvesicular cancer drug targeting SH-SY5Y neuroblastoma cancer, CAPE loading at a concentration of 5 μM to 100 μM is performed to the cellular microvesicles produced via the nerve cells; and these values are far more advantageous over the toxic high amounts of ≥100 μM applied in the previous individual CAPE applications in the literature.

The cancer drug product, which is produced by the CAPE loaded specialized cellular microvesicles obtained in the scope of the invention, has no toxic effect on healthy cells and other cell lines, while showing toxic effect only on a specific type of cancer. As shown in FIG. 1, and as mentioned above, the specialized microvesicles show cytotoxic effect only on SHSY5Y cells.

The inventive development of CAPE loaded microvesicular cancer drug targeting SH-SY5Y neuroblastoma cancer comprises the steps of Seeding (culturing) skin stem cells in a medium,
Implementing the specialization protocol, which enables the cells in a culture medium reaching sufficient confluency (70-80%) to be seeded in 6-well cell culture plates whereby the feature of neuroblastoma recognition is provided to the cells enabling them to become targeted,
Dissolving CAPE (caffeic acid phenethyl ester) in DMSO (Dimethyl sulfoxide) thereby preparing the stock solution (thus different concentrations can be obtained from the more concentrated stock solution),
Performing microvesicle isolation from the specialized skin cells,
Adding CAPE into the microvesicles,
Separating the CAPE loaded microvesicles from the CAPE which is free in the solution and not loaded to a microvesicle,
Obtaining the CAPE loaded microvesicular cancer drug targeting SH-SY5Y neuroblastoma cancer which is the final product.

In the preferred embodiment of the invention, during the step of carrying out the culturing of the skin stem cells; the skin stem cell, SH-SY5Y, PNT-1A, PC-3 cells are cultured preferably in DMEM (Dulbecco's Modified Eagle's Medium) medium containing 10% fetal bovine serum and 1% PSA in cell culture incubators preferably at 37° C. and 5% $CO_2$.

In the preferred embodiment of the invention, during the step of specializing the cells in the culture medium, a Neurobasal solution preferably containing 10 ng/ml bFGF, 10 ng/ml EGF, 1% B7 supplement, 1% ITS (insulin, transferrin and selenium), 10% Glutamine and 1% PSA is prepared and then the specialization protocol is applied by administering this specialization solution to the cells seeded in 6-well cell culture plates once in two days for 12 to 14 days.

In the preferred embodiment of the invention, in the step of preparing the stock solution, 45.75 mg of CAPE is preferably dissolved in 3.22 mL of DMSO (Dimethyl sulfoxide). The final concentration obtained is approximately 50,000 μM.

In the preferred embodiment of the invention, in the step of microvesicle isolation from the specialized skin cells, the solution collected from the culture medium is centrifuged at 300 g for 10 minutes to remove the waste cells. The supernatant remaining at the upper part of the tube after the centrifugation is transferred to a new tube and it is centrifuged at 14000 g for 30 minutes in order to remove possible cell components. The supernatant remaining at the upper part of the tube after the centrifugation is transferred to a new tube and ½ volume of solution A is added, and it is incubated for one day at +4 degrees. The next day, after it is centrifuged at 16000 g for 1 hour, the pellet is dissolved in distilled water ($dH_2O$).

In the preferred embodiment of the invention, loading CAPE into the microvascular structure is carried out by incubation at room temperature. Microvesicle solution is added to a 50 μM CAPE solution preferably prepared in 2 ml of PBS such that the final concentration will be 100 μg/ml, and the mixture is incubated for 20 minutes at room temperature (25° C.). Then, the precipitation process is carried out using the isolation kit to obtain the substance-loaded vesicles. The resulting substance-loaded pellet is dissolved in distilled water ($dH_2O$).

In the "CAPE loaded microvascular cancer drug targeting SHSY5Y neuroblastoma cancer (Micro-CAPE)" of the present invention, the skin stem cells, PNT-1A, PC-3 and SH-SY5Y cells are used. The toxicity of the targeted microvesicles, which are obtained by specialization of the stem cells, to the SH-SY5Y cells was observed. By loading CAPE to the microvesicles obtained in this study, a cell-specific targeted vesicle is developed while the toxicity to both the other cells and the body is minimized by using much lower concentrations of CAPE compared to the concentrations previously used in the literature.

Within the scope of the invention, first of all, the skin stem cells, SH-SY5Y, PNT-1A and PC-3 cells were cultured in Dulbecco's modified Eagle's medium (DMEM) containing 10% fetal bovine serum (Invitrogen) and 1% PSA (Biological Industries, Beit Haemek, Israel) at a temperature of 37° C. in cell culture incubators with 5% $CO_2$. The cells in the culture solution reaching sufficient confluence (70-80%) are seeded in 6-well culture plates and the specialization protocol is applied thereon for 13 days with Neurobasal solution containing 10 ng/ml bFGF, 10 ng/ml EGF, 1% B7 supplement, 1% ITS (insulin, transferrin and selenium), 10% Glutamine and 1% PSA by changing the media every other day. In the meantime, the process of preparing the stock solution is started. For this purpose, 45.75 mg of CAPE is dissolved in 3.22 mL of DMSO (Dimethyl sulfoxide). The final concentration obtained is 50.000Mµ.

Microvesicles are isolated from the skin cells on which specialization protocol is applied. EX01 Exo-Spin™ kit was used for microvesicle isolation from the specialized skin cells in the scope of the invention. The medium collected from the culture medium is centrifuged at 300 g for 10 minutes in order to remove the waste cells. The supernatant is transferred to a new tube and it is centrifuged at 14000 g for 30 minutes in order to remove possible cell components. The supernatant obtained by this centrifugation is transferred to a new tube and ½ volume of solution A is added, and it is incubated for one day at +4 degrees. The next day, after it is centrifuged at 16000 g for 1 hour, the pellet is dissolved in distilled water ($dH_2O$).

Loading of CAPE, which is prepared as a separate solution, into the microvesicles is carried out at room temperature. To a solution of 50 µM CAPE prepared in 2 ml PBS is added the microvesicle solution such that the final concentration will be 100 ug/ml. The mixture is incubated for 20 minutes at room temperature (25° C.) and then, the precipitation process is carried out using the isolation kit to obtain CAPE loaded vesicles. The resulting substance-loaded pellet is dissolved in distilled water ($dH_2O$).

By means of the inventive "Development of CAPE loaded microvesicular cancer drug targeting SHSY5Y neuroblastoma cancer (Micro-CAPE)", the drug is enabled
 to be used at much lower concentrations (5 µM),
 to be specific to cell type,
 to pass the blood-brain barrier,
 not to cause inflammation,
 not to have any toxicity to the body,
 to prevent resistance of the cancer type,
 to be metabolized in the cell after use,
 to remain in the circulation for a long time.

EXPERIMENTAL STUDIES

Measuring the Amount of CAPE that is Loaded

After the loading process, measurement of the amount of CAPE transferred into the microvesicular structure was performed based on the spectrophotometric measurement method. When measuring the amount of CAPE that was loaded, the intrinsic radiation of the molecule at 323 nm wavelength was utilized. Different concentrations (1-100 µM) of CAPE were measured at the wavelength of 323 nm to form a standard curve. The amount of CAPE that was loaded was determined using two interrelated methods. Firstly, the amount of CAPE that was loaded was determined by measuring the amount remaining in the supernatant after precipitation of the CAPE-loaded microvesicles. Secondly, it was determined by fractionation of the membrane structures of the microvesicles loaded with the precipitated substance, and measurement of the amount of CAPE loaded to the vesicular structure.

Determining Toxicity

After the cells were seeded in 96-well culture plates (Corning Glasswork, Corning, N.Y.) at 5000 cells/well in Dulbecco's modified Eagle's medium (DMEM) containing 10% fetal bovine serum (Invitrogen) and 1% PSA (Biological Industries, Beit Haemek, Israel) in the culture solution, the viability levels of the cells were measured on day 1, 2 and 3. Cell viability was determined by using 3-(4,5-dimethyl-thiazol-2-yl)-5-(3-carboxy-methoxy-phenethyl)-2-(4-sulfo-phenethyl)-2H-tetrazolium (MTS)-method (CellTiter96 AqueousOne Solution; Promega, Southampton, UK). 10 µl MTS solution was added onto the cells within a 100 µl medium and it was incubated at 37° C. in dark for 2 hours. After the incubation process, cell viability was observed by performing absorbance measurement via ELISA plate reader (Biotek, Winooski, Vt.) device at 490 nm wavelength.

REFERENCES

[1]. Lin, H. P., Lin, C. Y., Liu, C. C., Su, L. C., Huo, C., Kuo, Y. Y., Tseng, J. C., Hsu, J. M., Chen, C. K., Chuu, C. P. 2013. "Caffeic Acid phenethyl ester as a potential treatment for advanced prostate cancer targeting akt signaling", Int J Mol Sci., 6; 14(3):5264-83. doi: 10.3390/ijms14035264.

[2]. Tolba, M. F., Omar, H. A., Azab, S. S., Khalifa, A. E., Abdel-Naim, A. B., Abdel-Rahman, S. Z. 2014. "Caffeic acid phenethyl ester: A review of its antioxidant activity, protective effects against ischemia-reperfusion injury and drug adverse reactions", Crit Rev Food Sci Nutr., DOI: 10.1080/10408398.2013.821967.

[3]. Wu, J., Omene, C., Karkoszka, J., Bosland, M., Eckard, J., Klein, C. B., Frenkel, K. 2011. "Caffeic acid phenethyl ester (CAPE), derived from a honeybee product propolis, exhibits a diversity of anti-tumor effects in pre-clinical models of human breast cancer", Cancer Lett., 1; 308(1): 43-53. doi: 10.1016/j.canlet.2011.04.012.

[4]. Omene, C. O., Wu, J., Frenkel, K. 2012. "Caffeic Acid Phenethyl Ester (CAPE) derived from propolis, a honeybee product, inhibits growth of breast cancer stem cells", Invest New Drugs, 30(4):1279-88. doi: 10.1007/s10637-011-9667-8.

[5]. Chuu, C. P., Lin, H. P., Ciaccio, M. F., Kokontis, J. M., Hause, R. J. Jr, Hiipakka, R. A., Liao, S., Jones, R. B. 2012. "Caffeic acid phenethyl ester suppresses the proliferation of human prostate cancer cells through inhibition of p70S6K and Akt signaling networks", Cancer Prev Res (Phila)., 5(5):788-97. doi: 10.1158/1940-6207.CAPR-12-0004-T.

[6]. Hsu, T. H., Chu, C. C., Hung, M. W., Lee, H. J., Hsu, H. J., Chang, T. C. 2013. "Caffeic acid phenethyl ester induces E2F-1-mediated growth inhibition and cell-cycle arrest in human cervical cancer cells" FEBS J., 280(11): 2581-93. doi: 10.1111/febs.12242.

[7]. Kuo, Y. Y., Lin, H. P., Huo, C., Su, L. C., Yang, J., Hsiao, P. H., Chiang, H. C., Chung, C. J., Wang, H. D., Chang, J. Y., Chen, Y. W., Chuu, C. P. 2013. "Caffeic Acid Phenethyl Ester Suppresses Proliferation and Survival of TW2.6 Human Oral Cancer Cells via Inhibition of Akt Signaling", Int J Mol Sci., 24; 14(5):8801-17. doi: 10.3390/ijms14058801.

[8]. Kim, E. Y., Ryu, J. H., Kim, A. K. 2013. "CAPE promotes TRAIL-induced apoptosis through the upregulation of TRAIL receptors via activation of p38 and suppression of JNK in SK-Hep1 hepatocellular carcinoma cells", Int J Oncol., 43(4):1291-300. doi: 10.3892/ijo.2013.2018.

[9]. Yagmurca, M., Erdogan, H., Iraz, M., Songur, A., Ucar, M., Fadillioglu, E. 2004. "Caffeic acid phenethyl ester as a protective agent against doxorubicin nephrotoxicity in rats", Clin Chim Acta, 348:27-34.

[10]. Fadillioglu, E., Oztas, E., Erdogan, H., Yagmurca, M., Sogut, S., Ucar, M., et al. 2004. "Protective effects of caffeic acid phenethyl ester on doxorubicin-induced cardiotoxicity in rats", J Appl Toxicol, 24:47-52.

[11]. Irmak, M. K., Fadillioglu, E., Sogut, S., Erdogan, H., Gulec, M., Ozer, M., et al. 2003. "Effects of caffeic acid phenethyl ester and alpha-tocopherol on reperfusion injury in rat brain", Cell Biochem Funct., 21:283-9.

[12]. Iraz, M., Ozerol, E., Gulec, M., Tasdemir, S., Idiz, N., Fadillioglu, E., et al. 2006. "Protective effect of caffeic acid phenethyl ester (CAPE) administration on cisplatin-induced oxidative damage to liver in rat", Cell Biochem Funct., 24:357-61.

[13]. Akyol, S., Ginis, Z., Armutcu, F., Ozturk, G., Yigitoglu, M. R., Akyol, O. 2012. "The potential usage of caffeic acid phenethyl ester (CAPE) against chemotherapy-induced and radiotherapy-induced toxicity", Cell Biochem Funct., 30(5):438-43. doi: 10.1002/cbf.2817.

[14]. Yildiz, O. G., Soyuer, S., Saraymen, R., Eroglu, C. 2008. "Protective effects of caffeic acid phenethyl ester on radiation induced lung injury in rats", Clin Invest Med, 31: E242-7.

[15]. Izuta, H., Shimazawa, M., Tazawa, S., Araki, Y., Mishima, S., & Hara, H. 2008. "Protective effects of Chinese propolis and its component, chrysin, against neuronal cell death via inhibition of mitochondrial apoptosis pathway in SH-SY5Y cells", *Journal of Agricultural and Food Chemistry*, 56(19), 8944-8953.

[16]. Lee, H. Y., Jeong, Y. I., Kim, E. J., Lee, K. D., Choi, S. H., Kim, Y. J., . . . & Choi, K. C. 2015. "Preparation of Caffeic Acid Phenethyl Ester-Incorporated Nanoparticles and Their Biological Activity". *Journal of pharmaceutical sciences*, 104(1), 144-154.

What is claimed is:

1. A composition comprising a plurality of cellular vesicles loaded with caffeic acid phenethyl ester for inhibiting growth of the cancer cells, wherein the plurality of cellular vesicles are produced from PC-3 cells.

2. The composition according to claim 1, wherein the PC-3 cells from which the cellular vesicles are produced are cultured in Dulbecco's modified Eagle's medium (DMEM) at a temperature of 37° C. and under 5% carbon dioxide.

3. The composition according to claim 1, wherein the cellular vesicles are microvesicles.

\* \* \* \* \*